United States Patent
Hockersmith

(10) Patent No.: US 7,289,033 B2
(45) Date of Patent: Oct. 30, 2007

(54) WIRELESS SENSING WASHERS FOR IMAGING DEVICE ATTACHMENT

(75) Inventor: Ron K. Hockersmith, Waukesha, WI (US)

(73) Assignee: General Electric Co., Schenectady, NY (US)

( * ) Notice: Subject to any disclaimer, the term of this patent is extended or adjusted under 35 U.S.C. 154(b) by 373 days.

(21) Appl. No.: 11/160,618

(22) Filed: Jun. 30, 2005

(65) Prior Publication Data

US 2007/0025823 A1 Feb. 1, 2007

(51) Int. Cl.
*G08B 21/00* (2006.01)

(52) U.S. Cl. .................. 340/665; 340/668; 340/539.12; 600/439; 600/453; 378/4; 378/21; 382/128; 382/131

(58) Field of Classification Search ...................... None
See application file for complete search history.

(56) References Cited

U.S. PATENT DOCUMENTS

| | | | | |
|---|---|---|---|---|
| 6,055,329 | A | * | 4/2000 | Mufti .......................... 382/152 |
| 6,104,896 | A | * | 8/2000 | Zaman et al. ................ 399/117 |
| 6,204,771 | B1 | * | 3/2001 | Ceney ......................... 340/665 |
| 2006/0009856 | A1 | * | 1/2006 | Sherman et al. .......... 623/20.32 |

* cited by examiner

*Primary Examiner*—Julie Bichngoc Lieu

(57) ABSTRACT

A computed tomography assembly is provided comprising at least one clamped imaging component and a clamping fastener having a clamping head attached thereto. A load-sensing washer is positioned between the clamping head and the at least one clamped imaging component and includes a pressure sensor element in communication with a wireless transmitter transmitting a fastener load value. A wireless receiver is adapted to remotely receive the fastener load value and a processor in communication with the wireless receiver includes logic adapted to monitor the fastener load value in real time.

20 Claims, 2 Drawing Sheets

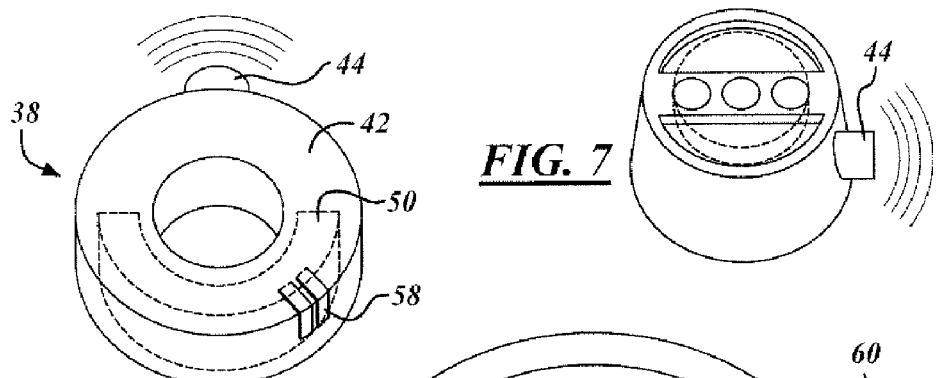
FIG. 4
FIG. 7
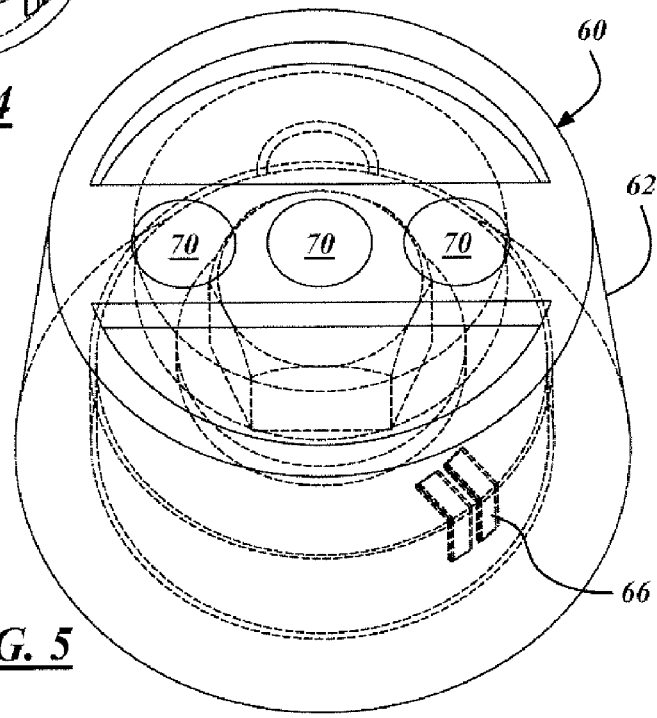
FIG. 5
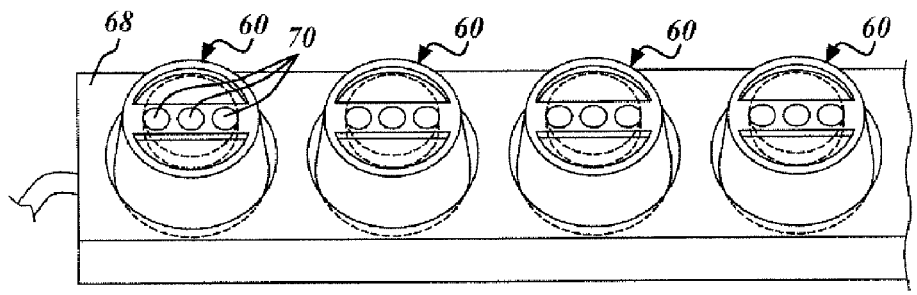
FIG. 6

WIRELESS SENSING WASHERS FOR IMAGING DEVICE ATTACHMENT

TECHNICAL FIELD

The present invention relates generally to a medical imaging assembly utilizing load-sensing washers and more particularly to load-sensing washers utilizing wireless transmission capabilities to reduce the complexity of the imaging assembly. In addition to reducing system complexity, the present invention provides increased confidence in critical components of the imaging system by utilizing real-time monitoring.

BACKGROUND OF THE INVENTION

Modern medical imaging assemblies, such as x-ray tubes, are becoming increasingly powerful as their respective technologies advance. In many cases, as the power of these assemblies increases so too does the mass of their respective components. This increase in mass can result in an increase in strain on individual components within the assembly. Components are often joined using bolted joints, which must bear the strain of these increases. The need to accommodate stress and strain increases impacts basic functioning, performance, and precision of the imaging assembly.

Additional complications arise in complex imaging technologies such as computed tomography (CT). Computed tomography assemblies commonly alternate loads and stresses on their components and bolted joints due to starting, stopping, and rotation of the system. This subjects these bolted joints to high and variable loading which in turn makes them susceptible to fatigue. The bolted joints in these systems can be highly critical as they are used to attach imaging devices to the rotating assembly portions of the CT assembly.

It is recognized that fatigue resistance of a bolted joint is primarily driven by the preload applied to the fastener by the torque applied during installation in combination with joint characteristics. Monitoring the real-time force present in a fastener would allow for detection of attachment problems prior to any failure of the system, joint, or component. A multitude of direct load monitoring techniques are known, but require a direct physical connection to the bolt joints. This, in turn, introduces a plurality of additional circuits, cumbersome wiring, complex interference reconfigurations, and increases slip ring issues. Thus direct physical connection monitoring has an undesirably effect of assembly complexity, configuration, and cost.

It would, therefore, be highly desirable to have an assembly for monitoring bolt or other fixture strain in medical imaging assemblies that had minimal impact of assembly complexity, configuration, and cost. Additionally, it would be highly desirable to have such an assembly that could communicate wirelessly between the fixture joints and a remote monitor to eliminate the need for complex wiring configurations.

SUMMARY OF THE INVENTION

A computed tomography assembly is provided comprising at least one clamped imaging component and a clamping fastener having a clamping head attached thereto. A load-sensing washer is positioned between the clamping head and the at least one clamped imaging component and includes a pressure sensor element in communication with a wireless transmitter transmitting a fastener load value. A wireless receiver is adapted to remotely receive the fastener load value and a processor in communication with the wireless receiver includes logic adapted to monitor the fastener load value in real time.

Other features of the present invention will become apparent when viewed in light of the detailed description of the preferred embodiment when taken in conjunction with the attached drawings and appended claims.

BRIEF DESCRIPTION OF THE DRAWINGS

FIG. 4 is a detailed illustration of a load sensing washer for use in the fastener assembly illustrated in FIG. 2.

FIG. 5 is an illustration of a removable charging cap for use with the fastener assembly illustrated in FIG. 2.

FIG. 6 is an illustration of a charging station for use with the charging cap illustrated in FIG. 5.

FIG. 7 is an illustration of a transmitter cap for use in place of the charging cap illustrated in FIG. 5.

DESCRIPTION OF THE PREFERRED EMBODIMENT(S)

Figure 1:
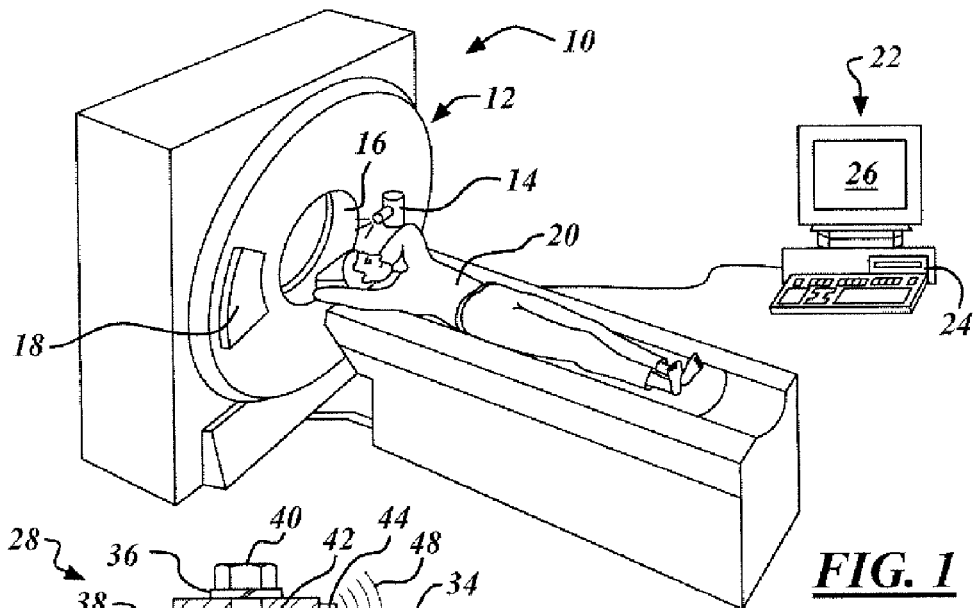
FIG. 1 is an illustration of an medical imaging assembly in accordance with the present invention.
Figure 2:
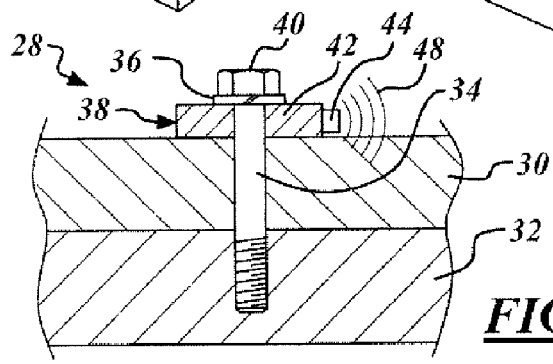
FIG. 2 is a detailed illustration of a fastener assembly for use in the medical imaging assembly illustrated in FIG. 1.

Referring now to FIG. 1, which is an illustration of a medical imaging assembly 10 or specifically a computed tomography (CT) imaging system 10 for use with the present invention. Although a particular CT imaging system 10 has been illustrated, it should be understood that the present invention may be utilized in a wide variety of imaging systems. The CT imaging system 10 includes a scanner assembly 12 illustrated as a gantry assembly. The scanner assembly 12 includes an x-ray source 14 for projecting a beam of x-rays 16 toward a detector assembly 18 positioned opposite the x-ray source 14. The detector assembly 18 senses the projected x-rays 16 that pass through an object, such as a medical patient 20. Commonly, during a scan to acquire x-ray projection data, the scanner assembly 12 is rotated about the patient 20. Data from the detector assembly 18 is subsequently processed to reconstruct a medical image or multiple images of the patient 20. A computer 22 is used receive commands and scanning parameters from an operator via console 24 that has a keyboard or similar input device. An associated display 26 allows the operator to observe the reconstructed image and other data from the computer 22. The resultant assembly 10 is subject to alternating loads and stresses on its components and bolted joints due to starting, stopping, and rotation of the system. The present invention addresses these concerns through the use of a novel fastener assembly 28 as is illustrated in FIG. 2.

The illustrated fastener assembly 28 is utilized to join or clamp a first clamping component 30 to a second clamping component 32. These clamping components 30, 32 are intended to include the vast number of critical components throughout the medical imaging assembly 10 whose performance is significant to operation or whose position or configuration makes them susceptible to fatigue or other performance altering conditions. A clamping fastener 34 and lock-washer 36 place the components 30,32 in clamped communication with each other. The present invention contemplates the use of a load sensing washer 38 positioned between the clamping head 40 of the clamping fastener 34 and one of the clamping components 30. In at least one embodiment, the lock-washer 36 is positioned between the clamping head 40 and the load-sensing washer 38. The load-sensing washer 38 is intended to encompass a washer containing a pressure sensor element 42 such as a pressure transducer or a piezoelectric sensor. Other load/pressure sensing elements may also come to mind in light of the present disclosure.

Figure 3:
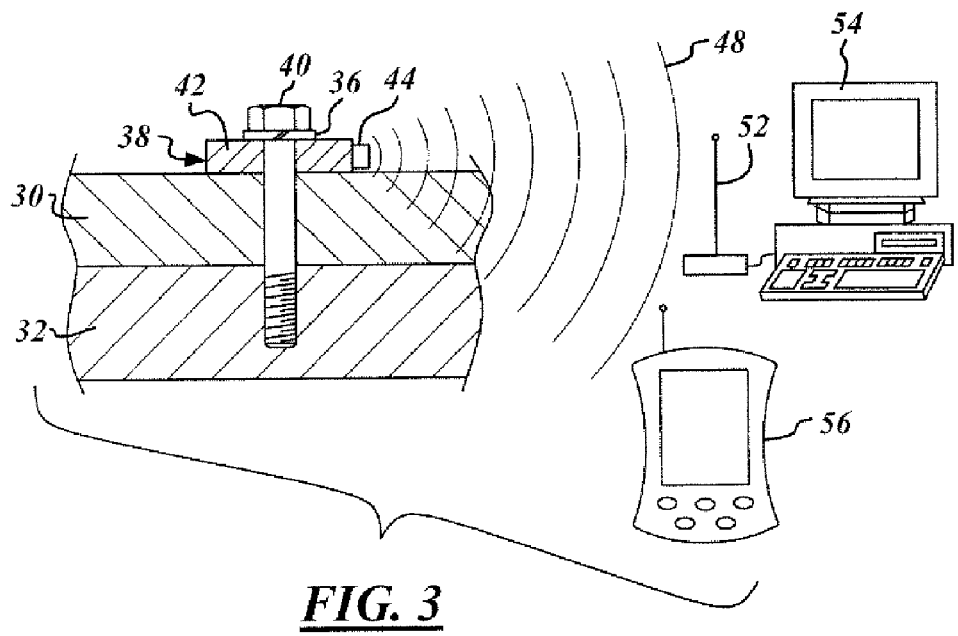
FIG. 3 is an illustration of the fastener assembly illustrated in FIG. 2, the fastener assembly illustrated in wireless communication with a remote processor.

The use of a simple pressure sensing washer alone would give rise to a number of complexity and configuration issues. This is because the number of fastener assemblies 28 and their locations throughout the medical imaging assembly 10 would give rise to unwieldy and costly wiring routes. The present invention, however, provides a unique solution to this undesirable complexity by further including a wireless transmitter 44 in communication with the pressure sensor element 42 such that the transmitter 44 can receive a fastener load value 48 from the sensor and transmit it to a remote location. The wireless transmitter 44 can be any of a wide variety of transmitters available to the wireless transmission market such as Bluetooth transmitters. The wireless transmitter 44 is preferably integrated directly into the load-sensing washer 38 for reduced complexity. It is further contemplated that the load-sensing washer 38 contains a washer internal battery 50 mounted within its interior by which to power the wireless transmitter (see FIG. 3).

The wireless transmitter 44 transmits the fastener load value 48 which in turn is received by a wireless receiver 52 in communication with a remote processor 54. In this fashion, the processor can provide real-time monitoring of a vast plurality of fastener load values 48, one for each installed fastener, and allow an operator or automated software to provide a warning if the value drops below an acceptable level. In this fashion, a real time monitoring of a vast plurality of fasteners is quickly an effectively accomplished in real-time. Additionally, the receiver 52 and processor 54 may be integrated into a hand held computing device 56 which may allow for reduced transmission distance and thereby reduced transmission strength. By reducing the required transmission strength, the transmission life of the load sensing washer 38 may be significantly increased. An additional energy saving features contemplates the integration of logic into the wireless transmitter 44 such that the transmitter 44 is only activated if the fastener load value 48 drops below a predetermined value such as a minimum performance load. This can be utilized to conserve the washer internal battery 50 and extend the usefulness of the load-sensing washer 38.

It is preferably, however, for the load-sensing washer 38 to provide constant readings of the fastener load value 48 such that a real-time assessment of performance may be measured. As such, the present invention contemplates the use of at least one external terminals 58 integrated in the washer 38 and in communication with the washer internal battery 50. This allows for the recharging of the washer internal battery 50 and therefore an extension of the performance life of the load-sensing washer 38. A removable charging cap 60 (see FIG. 4) may be used in combination to provide a convenient and reliable way of maintaining adequate charge in the washer internal battery 50. The removable charging cap 60 would comprise a charging housing 62 containing a charging battery 64 contained therein. The charging battery 64 is in communication with at least one charging terminal 66 orientated within the housing 62 such that it coincides with the external terminals 58 on the load sensing washer 38. The housing 62 is preferably adapted to fit over clamping head 40 and is frictionally held in place. A charging station 68 may be used to keep a plurality of removable charging caps 60 fully charged and ready for use. An operator may thereby remove the removable charging cap 60 from the charging station 68 and place it into communication with the load-sensing washer 38. Charging status indicators 70 are mounted on the charging housing 62 and preferably serve a dual purpose. When on the charging station 68, the indicators 70 communicate the charging status of the charging battery 64. When in communication with the load-sensing washer 38, the indicators 70 indicate the charging status of the washer internal battery 50.

It is contemplated that in operation, the removable charging caps 60 may be used in a variety of fashions. In one embodiment, they may be placed on the load sensing washers 38 during periods of non-use of the medical imaging assembly. In another contemplated scenario, an operator may install them on a schedule suitable for maintaining acceptable charges. Finally, it is contemplated that the wireless transmitter 44 may further include logic sending a signal when the charge of the washer internal battery 50 is too low, thereby alerting an operator to install the charging cap 60. The charging caps 70 may even be designed to maintain a small enough profile so as to be left on for extended periods of time during machine operation.

In light of the last described embodiment, the present invention further contemplates an embodiment illustrated in FIG. 7, wherein the wireless transmitter 44 is moved into a removable transmitter cap 72 and an un-powered battery free load sensing washer 38 may be utilized. In this case, the transmitter cap 72 includes a transmitter battery 74 positioned within a transmitter housing 76. By placing the transmitter cap 72 into communication with the load-sensing washer 38, the wireless transmitter 44 is placed into communication with the pressure sensor element 42. In this fashion, the caps 72 may be again kept on a charging station 68 and installed onto the load-sensing washers 38 whenever real-time monitoring of loading is required.

While particular embodiments of the invention have been shown and described, numerous variations and alternative embodiments will occur to those skilled in the art. Accordingly, it is intended that the invention be limited only in terms of the appended claims.

What is claimed is:

1. A computed tomography assembly comprising:
   at least one clamped imaging component:
   a clamping fastener attached to said at least one clamped imaging component, said clamping fastener including a clamping head;
   a load-sensing washer positioned between said clamping head and said at least one clamped imaging component, said load-sensing washer comprising:
   a pressure sensor element; and
   a wireless transmitter in communication with said pressure sensor element, said wireless transmitter transmitting a fastener load value received from said pressure sensor element;
   a wireless receiver adapted to remotely receive said fastener load value; and
   a processor in communication with said wireless receiver, said processor including logic adapted to monitor said fastener load value in real time.

2. A computed tomography assembly as described in claim 1, wherein said pressure sensor element is taken from the group of pressure transducers and piezoelectric sensors.

3. A computed tomography assembly as described in claim 1, wherein said wireless transmitter includes logic adapted to only transmit said fastener load value when said fastener load value drops below a minimum threshold value.

4. A computed tomography assembly as described in claim 1, wherein said processor comprises a hand-held computing device.

5. A computed tomography assembly as described in claim 1, wherein said load-sensing washer comprise a washer internal battery positioned within a washer outer surface; and at least one external terminal formed on said washer outer surface, said at least one external terminal in communication with said washer internal battery.

6. A computed tomography assembly as described in claim 5, further comprising:
at least one removable charging cap, said removable charging cap comprising:
a charging housing adapted to be positioned and secured over said clamping head;
a charging battery positioned within said charging housing; and
a charging terminal adapted to engage said external terminal when said removable charging cap is positioned over said clamping head, said charging battery recharging said washer internal battery.

7. A computed tomography assembly as described in claim 6, further comprising:
a charging station positioned remotely from said clamping fastener, said removable charging cap positioned on and receiving recharging from said charging station when said removable charging cap is not positioned on said clamping head.

8. A computed tomography assembly as described in claim 6, further comprising:
a charge status indicator panel positioned on said removable charging cap, said charge status indicator panel providing visual status of said washer internal battery.

9. A medical imaging assembly comprising:
at least one clamped imaging component:
a clamping fastener attached to said at least one clamped imaging component, said clamping fastener including a clamping head;
a load-sensing washer positioned between said clamping head and said at least one clamped imaging component, said load-sensing washer including a pressure sensor element;
a wireless transmitter in communication with said pressure sensor element, said wireless transmitter transmitting a fastener load value received from said pressure sensor element; and
a wireless receiver adapted to remotely receive said fastener load value.

10. A medical imaging assembly as described in claim 9, wherein said wireless transmitter includes logic adapted to only transmit said fastener load value when said fastener load value drops below a minimum threshold value.

11. A medical imaging tomography assembly as described in claim 9, wherein said load-sensing washer comprises a washer internal battery positioned within a washer outer surface.

12. A medical imaging tomography assembly as described in claim 9, further comprising:
at least one removable transmitter cap, said removable transmitter cap comprising:
a transmitter housing adapted to be positioned and secured over said clamping head, said wireless transmitter positioned within said transmitter housing;
a transmitter battery positioned within said transmitter housing, said removable transmitter cap in removable communication with said pressure sensor element when said removable transmitter cap is positioned over said clamping head such that said fastener load value is communicated from said pressure sensor element to said wireless transmitter.

13. A medical imaging assembly as described in claim 12, further comprising:
a charging station positioned remotely from said clamping fastener, said removable transmitter cap positioned on and receiving recharging from said charging station when said removable transmitter cap is not positioned on said clamping head; and
a charge status indicator panel positioned on said removable transmitter cap, said charge status indicator panel providing visual status of said transmitter battery.

14. A medical imaging assembly as described in claim 9, wherein said wireless receiver is position within a hand held computing device.

15. A medical imaging assembly as described in claim 9, wherein said pressure sensor element comprises an un-powered sensor element.

16. A method of monitoring fastener load in a medical imaging assembly, comprising:
positioning a load sensing washer between a clamping fastener and at least clamped imaging component;
loading said clamping fastener;
measuring said loading using a pressure sensor element positioned within said load-sensing washer to generate a fastener load value;
transmitting said fastener load value using a wireless transmitter in communication with said pressure sensor element;
receiving said fastener load value using a wireless receiver positioned remotely from said load sensing washer; and
monitoring said fastener load value in real time using a processor in communication with said wireless receiver.

17. A method as described in claim 16, further comprising:
utilizing logic to only transmit said fastener load value when said fastener load value drops below a minimum threshold value.

18. A method as described in claim 16, further comprising:
embedding said wireless transmitter into said load-sensing washer.

19. A method as described in claim 18, further comprising:
charging at least one removable charging cap on a charging station;
removing said removable charging cap from said charging station; and
positioning said removable charging cap over said clamping fastener such that a charging terminal positioned on said removable charging cap engages an external terminal on said load-sensing washer;
charging a washer internal battery positioned within said load-sensing washer using said removable charging cap.

20. A method as described in claim 16, further comprising:
positioning a removable transmitter cap over said clamping fastener such that said load-sensing washer is placed in communication with said wireless transmitter, said wireless transmitter positioned in said removable transmitter cap;
powering said wireless transmitter using a transmitter battery positioned within said removable transmitter cap.

* * * * *